United States Patent
Johansson

(10) Patent No.: US 8,785,391 B2
(45) Date of Patent: Jul. 22, 2014

(54) COMPOUND AND METHOD FOR TREATMENT OF ALZHEIMER'S DISEASE AND FAMILIAL DEMENTIA

(75) Inventor: Jan Johansson, Stockholm (SE)

(73) Assignee: Alphabeta AB, Djursholm (SE)

( * ) Notice: Subject to any disclaimer, the term of this patent is extended or adjusted under 35 U.S.C. 154(b) by 0 days.

(21) Appl. No.: 13/805,574

(22) PCT Filed: Jun. 24, 2010

(86) PCT No.: PCT/SE2010/050723
§ 371 (c)(1),
(2), (4) Date: Mar. 7, 2013

(87) PCT Pub. No.: WO2011/162655
PCT Pub. Date: Dec. 29, 2011

(65) Prior Publication Data
US 2013/0172262 A1   Jul. 4, 2013

(51) Int. Cl.
C07K 14/47 (2006.01)
C07K 16/18 (2006.01)
A61K 38/48 (2006.01)
A61K 49/00 (2006.01)
G01N 33/53 (2006.01)
A61K 9/00 (2006.01)
A61K 38/00 (2006.01)

(52) U.S. Cl.
CPC ............... *C07K 14/47* (2013.01); *A61K 9/0019* (2013.01); *C07K 14/4711* (2013.01); *A61K 38/00* (2013.01)
USPC ....... 514/17.8; 514/17.7; 514/21.2; 514/21.3; 530/324; 530/350; 424/172.1; 435/7.1

(58) Field of Classification Search
None
See application file for complete search history.

(56) References Cited

U.S. PATENT DOCUMENTS

| | | | |
|---|---|---|---|
| 8,211,442 B2 | 7/2012 | Kido et al. | 424/204.1 |
| 8,268,321 B2 | 9/2012 | Kido et al. | 424/184.1 |
| 2003/0224982 A1 | 12/2003 | Li et al. | 514/12 |
| 2007/0141073 A1 | 6/2007 | Kido et al. | 424/185.1 |
| 2009/0130131 A1 | 5/2009 | Kido et al. | 424/185.1 |
| 2012/0122794 A1 | 5/2012 | Johansson | 514/17.8 |

FOREIGN PATENT DOCUMENTS

| | | | | |
|---|---|---|---|---|
| WO | WO 88/03170 | 5/1988 | | C12P 21/00 |
| WO | WO 02/41002 | 5/2002 | | G01N 33/68 |
| WO | WO 03/090682 | 11/2003 | | |
| WO | WO 2004/056310 | 7/2004 | | |

(Continued)

OTHER PUBLICATIONS

Shimshek et al., The HSP70 molecular chaperone is not beneficial in a mouse model of alpha-synucleinopathy. PLoS One, (Apr. 2010) 5(4):e10014.*

(Continued)

*Primary Examiner* — Gregory S Emch
*Assistant Examiner* — Aurora M Fontainhas
(74) *Attorney, Agent, or Firm* — Harness, Dickey & Pierce, P.L.C.

(57) ABSTRACT

An isolated protein is provided for use in treatment of a condition selected from the group consisting of Alzheimer's disease, familial Danish dementia and familial British dementia in a mammal, including man. The isolated protein is selected from the group consisting of proteins comprising an amino acid sequence having at least 70% identity to residues 90-236 of Bri2 from human; and proteins comprising an amino acid sequence having at least 70% identity to any one of the Brichos domains of Bri2 from human, chimpanzee, bovine, pig, mouse and rat.

13 Claims, 7 Drawing Sheets

(56) References Cited

FOREIGN PATENT DOCUMENTS

| WO | WO 2005/055994 | 6/2005 | ............ A61K 31/00 |
|---|---|---|---|
| WO | WO 2005/097182 | 10/2005 | ............ A61K 39/39 |
| WO | WO 2006/138355 | 12/2006 | ............ A61K 38/17 |
| WO | WO 2007/005672 | 1/2007 | |
| WO | WO 2007/018152 | 2/2007 | ............ A61P 37/08 |
| WO | WO 2008/066734 | 6/2008 | .......... A01K 67/027 |
| WO | WO 2008/151235 | 12/2008 | |
| WO | WO 2009/009396 | 1/2009 | ............ C07K 14/47 |
| WO | WO 2010/087771 | 8/2010 | ............ A61K 38/17 |

OTHER PUBLICATIONS

Citron, Alzheimer's disease: strategies for disease modification. Nat. Rev. Drug Discov. (2010) 9(5):387-398.*

Chaudhuri et al., Protein-misfolding diseases and chaperone-based therapeutic approaches. FEBS J. 2006, 273:1331-1349.*

Klucken et al., Hsp70 reduces alpha-synuclein aggregation and toxicity. (2004) J. Biol. Chem. 279(24):25497-25502.*

International Preliminary Report on Patentability for PCT/SE2010/050723 dated Dec. 28, 2012.

Accession No. Q3T0P7, Jan. 24, 2006 [online] [retreived on Jan. 26, 2011] Retrieved from EBI; Database UniProt,<URL: http://srs.ebi.ac.uk/srsbin/cgi-bin/wgetz?-e+[uniprotid:ITM2B_BOVIN]I-[uniprot-acc:ITM2B_BOVIN]+-noSession>.

Accession No. Q52N47, Jul. 24, 2007 [online] [retreived on Jan. 26, 2011] Retrieved from EBI; Database UniProt, <URL: http://srs.ebi.ac.uk/srsbin/cgi-bin/wgetz?-e+[uniprotid:ITM2B_PIG]I[uniprot-acc:ITM2B_PIG]+-noSession>; whole document; abstract.

Accession No. O89051, Jul. 15, 1999 [online] [retreived on Jan. 26, 2011] Retrieved from EBI; Database UniProt, <URL: http://srs.ebi.ac.uk/srsbin/cgi-bin/wgetz?-e+[uniprotid:ITM2B_MOUSE]I[uniprot-acc:ITM2B_MOUSE]+noSession>; whole document; abstract.

Accession No. Q5XIE8, Jan. 24, 2006 [online] [retreived on Jan. 26, 2011] Retrieved from EBI; Database UniProt, <URL:http://srs.ebi.ac.uk/srsbin/cgi-bin/wgetz?-e+[uniprotid:ITM2B_RAT]I[uniprot-acc:ITM2B_RAT]+-noSession>; whole document abstract.

DebBurman, S., et al. (1997) "Chaperone-supervised conversion of prion protein to its protease-resistant form" Proceeding of the National Academy of Science, 94:13938-13943.

Evans, C., et al. (2006) "Heat shock proteins 70 and 90 inhibit early stages of amyloid β-(1-42) aggregation in vitro" The Journal of Biological Chemistry, 281(44):33182-33191.

Fotinopoulou, A., et al. (2005) "BRI2 Interacts with amyloid precursor protein (APP) and regulates amyloid β (Aβ) production" The Journal of Biological Chemistry, 280(35): 30768-30772.

Hellstrand, E., et al. (2010) "Amyloid β-protein aggregation produces highly reproducible kinetic data and occurs by a two-phase process" ACS Chemical Neuroscience, 1:13-18.

Kim, J., et al. (2008) "BRI2(ITM2b) inhibits Aβ deposition in vivo" The Journal of Neuroscience, 28(23):6030-6036.

Martin, L., et al. (2008) "Regulated intramembrane proteolysis of Bri2 (Itm2b) by ADAM10 and SPPL2a/SPPL2b" The Journal of Biological Chemistry, 283(3):1644-1652.

Matsubara, E., et al. (1996) "Apolipoprotein J and alzheimer's amyloid β solubility" Biochemical Journal, 316:671-679.

Matsuda, S., et al. (2009) "Maturation of BRI2 generates a specific inhibitor that reduces APP processing at the plasma membrane and in endocytic vesicles" Neurobiology of Aging, 7384:1-9.

McHattie, S., et al. (1999) "Clusterin prevents aggregation of neuropeptide 106-126 in vitro" Biochemical and Biophysical Research Communications, 259:336-340.

Peng, S., et al. (2010) "The extracellular domain of Bri2 (ITM2B) binds the ABri peptide (1-23) and amyloid β-peptide (Aβ1-40): Implications for Bri2 effects on processing of amyloid precursor protein and Aβ aggregation" Biochemical and Biophysical Research Communications, 393:356-361.

Sánchez-Pulido, L., et al. (2002) "BRICHOS: a conserved domain in proteins associated with dementia, respiratory distress and cancer" Trends in Biochemical Sciences, 27(7):329-332.

Tomidokoro, Y., et al. (2005) "Familial Danish dementia co-existence of Danish and Alzheimer amyloid subunits (ADan and Aβ) in the absence of compact plaques" The Journal of Biological Chemistry, 280(44):36883-36894.

International Search Report for PCT/SE2010/050723 dated Feb. 3, 2011.

International Preliminary Report on Patentability dated Oct. 8, 2013 for International Appl. No. PCT/SE2012/050352.

Office Action dated Jan. 16, 2014 issued in U.S. Appl. No. 14/009,360.

Casals, C., et al. (2008), C-terminal, endoplasmic reticulum-lumenal domain of prosurfactant protein C-structural features and membrane interactions, The FEBS Journal, 1-12.

Chaudhuri, T., et al. (2006), "Protein-misfolding diseases and chaperone-based therapeutic approaches", The FEBS Journal, 273: 1331-1349.

Citron, M. (2010), "Alzheimer's disease: strategies for disease modification", Nature Reviews, 9: 387-398.

Fitzen, M., et al. (2009), "Peptide-binding specificity of the prosurfactant protein C brichos domain analyzed by electrospray ionization mass spectrometry", Rapid Communications in Mass Spectrometry, 23: 3591-3598.

Johansson, J. (2003), "Molecular determinants for amyloid fibril formation: lessons from lung surfactant protein C", Swiss Med Wkly, 133: 275-282.

Johansson, J., et al. (2006), "The brichos domain-containing C-terminal part of pro-surfactant protein C binds to an unfolded poly-val-transmembrane segment", The Journal of Biological Chemistry, 281(30): 21032-21039.

Johansson, H., et al. (2009), "Preventing amyloid formation by catching unfolded transmembrane segments", J. Mol. Biol., 389: 227-229.

Klucken, J., et al. (2004), "Hsp70 reduces α-synuclein aggregation and toxicity", The Journal of Biological Chemistry, 279(4): 25497-25502.

Nerelius, C., et al. (2008), "Mutations Linked to interstitial lung disease can abrogate anti-amyloid function of prosurfactant protein C", Biochem J., 416: 201-209.

Nerelius, C., et al. (2009), "Anti-amyloid activity of the C-terminal domain of proSP-C against amyloid β-peptide and medin", Biochemistry, 48: 3778-3786.

Nerelius, C., et al. (2010), "Amino Acid sequence determinants and molecular chaperones in amyloid fibril formation", Biochemical and Biophysical Research Communications, 396: 2-6.

Shimshek, D., et al. (2010), "The HSP70 molecular chaperone is not beneficial in a mouse model of α-synucleinopathy", PLoS ONE, 5(4): e10014.

Thompson, J., et al. (1994), "Clustal W: improving the sensitivity of progressive multiple sequence alignment through sequence weighting, position-specific gap penalties and weight matrix choice", Oxford University Press, 22(22): 4673-4680.

Vickers, J., (2002), "A vaccine against alzheimer's disease", Drugs Aging, 19(7):487-494.

Westermark, P., (2005), "Aspects on human amyloid forms and their fibril polypeptides", The FEBS Journal, 5942-5949.

Office Action dated Oct. 15, 2012 issued in U.S. Appl. No. 13/145,096.

Office Action dated Feb. 27, 2013 issued in U.S. Appl. No. 13/145,096.

Office Action dated Aug. 29, 2013 issued in U.S. Appl. No. 13/145,096.

Extended European Search Report dated Jul. 27, 2009 issued in EP Application No. 09151790.4.

International Search Report and Written Opinion dated Mar. 18, 2010 issued in PCT Application No. PCT/SE2010/050097.

International Preliminary Report on Patentability dated Sep. 15, 2010 issued in PCT Application No. PCT/SE2010/050097.

International Search Report dated Sep. 11, 2012 issued in PCT Application No. PCT/SE2012/050352.

* cited by examiner

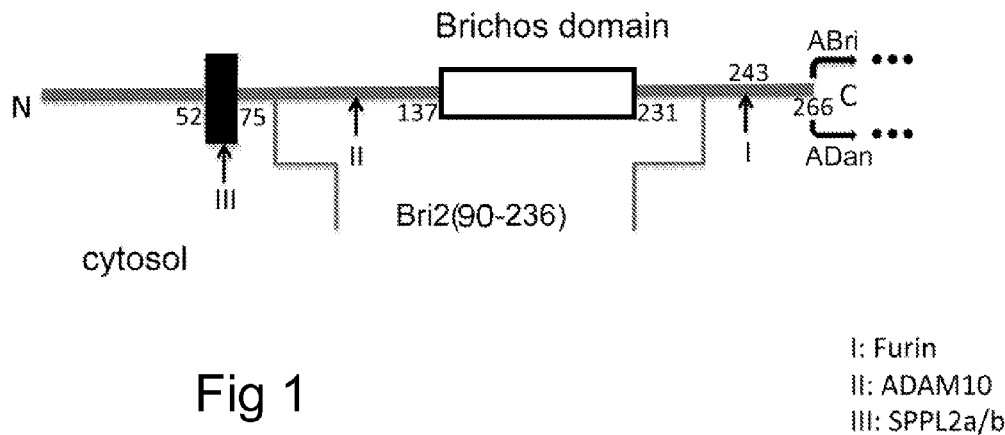

Fig 1

I: Furin
II: ADAM10
III: SPPL2a/b

```
Human    FADSDPANIVHDFNKKLTAYLDLNLDKCYVIPLNTSIVMPPRNLLELLIN
Chimp    FADSDPANIVHDFNKKLTAYLDLNLDKCYVIPLNTSIVMPPRNLLELLIN
Bovine   FADSDPANIVHDFNKKLTAYLDLNLDKCYVIPLNTSIVMPPKNLLELLIN
Pig      FADSDPANIVHDFNKKLTAYLDLNLDKCYVIPLNTSIVMPPRNLLELLIN
Mouse    FADSDPANIVHDFNKKLTAYLDLNLDKCYVIPLNTSIVMPPKNLLELLIN
Rat      FADSDPANIVHDFNKKLTAYLDLNLDKCYVIPLNTSIVMPPRNLLELLIN
Non-id                                            *

Human    IKAGTYLPQSYLIHEHMVITDRIENIDHLGFFIYRLCHDKETYKL
Chimp    IKAGTYLPQSYLIHEHMVITDRIENIDHLGFFIYRLCHDKETYKL
Bovine   IKAGTYLPQSYLIHEHMVITDRIENIDHLGFYIYRLCHDKETYKL
Pig      IKAGTYLPQSYLIHEHMVITDRIENIDHLGFYIYRLCHDKETYKL
Mouse    IKAGTYLPQSYLIHEHMVITDRIENVDNLGFFIYRLCHDKETYKL
Rat      IKAGTYLPQSYLIHEHMVITDRIENVDHLGFFIYRLCHDKETYKL
Non-id                            *       *
```

Fig 2

COMPOUND AND METHOD FOR TREATMENT OF ALZHEIMER'S DISEASE AND FAMILIAL DEMENTIA

PRIORITY STATEMENT

This application is a national phase application under 35 U.S.C. §371 of PCT International Application No. PCT/SE2010/050723 which has an International filing date of 24 Jun. 2010. The content of PCT/SE2010/050723 is incorporated herein by reference in its entirety.

FIELD OF THE INVENTION

The present invention pertains to the field of medicine. More specifically, this invention relates to medicaments for treatment and medical treatment of Alzheimer's disease, familial Danish dementia and familial British dementia in mammals, such as man.

BACKGROUND TO THE INVENTION

An increasing number of neurodegenerative conditions are linked to protein misfolding and aggregation, such as Alzheimer's disease and familial British or Danish dementia. These diseases are characterized by protein deposits in the brain parenchyma and cerebral arteries, and occur in inherited and sporadic forms. Even though these diseases have different clinical symptoms, they share some common pathological features, such as neuronal loss, protein aggregates, and presence of tau tangles. From a biochemical point of view, the proteins involved have a tendency to form β-sheet structures and are prone to aggregate into amyloid fibrils. Alzheimer's disease and familial British or Danish dementia display several similar neuropathological hallmarks. Amyloid plaques, neurofibrillary tangles, Congophilic amyloid angiopathy and neurodegeneration are observed.

Alzheimer's disease is one of the most common causes of dementia in man. It is a chronic and fatal disease associated with neural cell degeneration in the brain of the affected individual, characterized by the presence of amyloid plaques consisting of extracellular deposits of amyloid β-peptide (Aβ-peptide). The neural cell atrophy caused by Aβ aggregation results in deficiency of acetylcholine and other signaling substances. It is known that Aβ-peptide, having 40-42 amino acid residues, is produced by processing of the amyloid precursor protein (APP, 695-770 amino acid residues), which is a type I membrane protein normally expressed by the neurons of the central nervous system, but the reasons for this processing are incompletely understood. The released Aβ peptide contains a part of the transmembrane region of APP (Aβ residues 29-40/42) and includes a discordant helix, i.e. a helix composed of amino acids with a high propensity to form β-strands. Aβ is prone to misfold and aggregate when removed from its stabilising membrane environment.

Bri2 (SEQ ID NO: 1, also referred to as integral membrane protein 2B, ITM2B), is a 266-residue type II membrane protein (FIG. 1) with ubiquitous expression, whose function and folded structure are unknown. Bri2 is proteolytically cleaved at three locations; cleavage by furin in the C-terminal region generates a 23-residue peptide (ABri23), processing of the ectodomain by ADAM10 results in release of the Brichos domain from the membrane-bound N-terminal part, and intramembrane cleavage by SPPL2a/2b liberates the intracellular domain. Familial British and Danish dementia are caused by mutations in the Bri2 gene that result in a loss of a stop codon, which in turn results in two different 11-residue extensions of the C-terminal part, and, after furin cleavage, generation of 34-residue peptides (ABri and ADan, respectively) instead of the normally released ABri23. The longer peptides are prone to aggregation into amyloid fibrils and deposition in brain tissue or cerebral vessels, with concomitant neuronal loss and dementia.

Recent studies have shown that Bri2 and Aβ co-localize in amyloid plaques in brain parenchyma and vessels, suggesting that the proteins interact at some stage during misfolding and aggregation. Using transfected cell lines, Bri2 has been found to interact with APP, and to modulate APP processing by increasing β-secretase generated fragments. Generation of a fusion protein containing Bri2 and Aβ40 indicates that the Bri protein can affect Aβ aggregation properties, and using a transgenic mouse model, ABri23 has been proposed to interact with Aβ42 and prevent its aggregation (Kim et al. J. Neurosci. 28: 6030-6036 (2008); WO 2009/009396). It has also been suggested that Aβ production can be reduced or prevented by a protein containing the first 102 amino acid residues of Bri2 (WO 2006/138355).

Current therapeutic approaches for treatment of Alzheimer's disease are mainly directed to treating the symptoms and include cholinergic replacement therapy, e.g. inhibition of acetylcholinesterase, small inhibitors that interact with soluble Aβ oligomers, and so-called β-sheet breakers that prevent elongation of already formed β-sheet structures Another suggested strategy to prevent aggregation has been to utilize molecules that are functionally defined as chaperones. Chaperones play an important role by aiding the correct folding of proteins in the complex intracellular milieu. A number of molecular chaperones, such as heat-shock proteins (Hsp), are known to be important in the folding process and have been extensively studied. Some of these chaperones are apparently able to interact with and have an impact on the amyloid fibril formation of certain polypeptides. Aggregation of $A\beta_{1-42}$ is inhibited by Hsp90 or the combination Hsp70/Hsp40 (C G Evans et al, J Biol Chem 281: 33182-33191, 2006). Furthermore, the extracellular chaperone clusterin (apolipoprotein J) has been shown to inhibit fibril formation of a number of polypeptides including Aβ (E Matsubara et al, Biochem J 316(Pt 2): 671-679, 1996) and a fragment of the prion protein (S McHattie and N Edington, Biochem Biophys Res Commun 259: 336-340, 1999). The role of the structurally diverse chaperones in prevention of amyloid diseases is not established and some reports even indicate that protein chaperones promote amyloid fibril formation, see e.g. SK DebBurman et al. Proc Nat Acad Sci USA 94: 13938-13943, 1997. In addition to molecular chaperones, the effects of chemical and pharmacological chaperones have been studied in the context of misfolding diseases. No effective therapy using chaperones or other means has so far been found for any amyloid disease.

Monoclonal antibodies against Aβ peptide prevent aggregation into neurotoxic fibrils and dissolve already formed amyloid. However, antibody therapy is very costly and associated with side-effects of varying seriousness. Vaccination with β-amyloid in transgenic mice models of Alzheimer's disease has shown a significant reduction in the number of amyloid plaques and overall amyloid burden and even some improvement in cognitive performance.

SUMMARY OF THE INVENTION

It is an object of the invention to decrease aggregation of Aβ-peptide into amyloid fibrils.

It is also an object of the invention to decrease formation of amyloid plaques consisting of extracellular deposits of Aβ-peptide in the brain of a mammal.

It is another object of the invention to provide a new treatment option for the treatment of Alzheimer's disease in a mammal, including man.

It is also an object of the invention to provide a new treatment option for the treatment of familial Danish dementia and/or familial British dementia in a mammal, including man.

For these and other objects that will be evident from the following description, the present invention provides according to a first aspect an isolated protein selected from the group of proteins consisting of residues 90-236 of Bri2 from human (SEQ ID NO: 2) and the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10).

It has surprisingly been found that this isolated protein has the capacity to decrease amyloid fibril formation and/or reduce aggregation of Aβ-peptide. This is particularly surprising in view of the structural dissimilarity between the targets ABri23 (SEQ ID NO: 4) and Aβ peptide (SEQ ID NOS: 11-12). The present invention is based on the herein disclosed, surprising insights about the previously unknown substrate specificity of this isolated protein, which protein is encompassing the Brichos domain of Bri2, but not the ABri23 sequence.

In one embodiment, the isolated protein is selected from the group of proteins consisting of residues 90-236 of Bri2 from human (SEQ ID NO: 2); and the Brichos domain of Bri2 from human (SEQ ID NO: 5). In specific embodiments, the isolated protein is consisting of residues 90-236 of Bri2 from human (SEQ ID NO: 2) or the Brichos domain of Bri2 from human (SEQ ID NO: 5).

The isolated protein according to the invention is useful as a medicament, specifically in treatment of a condition selected from the group consisting of Alzheimer's disease, familial Danish dementia and familial British dementia in a mammal, including man. In a preferred embodiment, the isolated protein according to the invention is useful in treatment of Alzheimer's disease.

The present invention provides according to another aspect an isolated protein selected from the group consisting of proteins comprising an amino acid sequence having at least 70% identity to residues 90-236 of Bri2 from human (SEQ ID NO: 2); and proteins comprising an amino acid sequence having at least 70% identity to any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10); with the provisos that said protein is not comprising an amino acid sequence having at least 70% identity to residues 1-89 of Bri2 from human (SEQ ID NO: 3); and said protein is not comprising an amino acid sequence having at least 70% identity to human ABri23 (SEQ ID NO: 4); for use in treatment of a condition selected from the group consisting of Alzheimer's disease, familial Danish dementia and familial British dementia in a mammal, including man. In a preferred embodiment, the isolated protein according to the invention is useful in treatment of Alzheimer's disease.

In one embodiment, the isolated protein for use according to the invention is selected from the group consisting of proteins comprising an amino acid sequence having at least 70% identity to residues 90-236 of Bri2 from human (SEQ ID NO: 2); and proteins comprising an amino acid sequence having at least 70% identity to the Brichos domain of Bri2 from human (SEQ ID NO: 5).

In an embodiment, the isolated protein for use according to the invention is selected from the group consisting of proteins comprising an amino acid sequence having at least 90% identity to any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10). In specific embodiments, the isolated protein for use according to the invention is selected from the group consisting of proteins comprising any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10).

In certain embodiments, the isolated protein for use according to the invention is consisting of less than or equal to 200 amino acid residues, such as less than or equal to 150 amino acid residues. In certain embodiments, the isolated protein for use according to the invention is consisting of more than or equal to 90 amino acid residues.

According to a related aspect, the present invention provides use of an isolated protein according to the invention for the manufacture of a medicament for the treatment of a condition selected from the group consisting of Alzheimer's disease, familial Danish dementia and familial British dementia in a mammal, including man. In a preferred embodiment, the condition is Alzheimer's disease.

According to a related aspect, the present invention provides a pharmaceutical composition comprising a therapeutically effective amount of an isolated protein according to the invention and a suitable pharmaceutical carrier therefor. The pharmaceutical composition is useful as a medicament, specifically in treatment of a condition selected from the group consisting of Alzheimer's disease, familial Danish dementia and familial British dementia in a mammal, including man. In a preferred embodiment, the pharmaceutical composition according to the invention is useful in treatment of Alzheimer's disease.

According to another aspect, the present invention provides a method of treating a condition selected from the group consisting of Alzheimer's disease, familial Danish dementia and familial British dementia in a mammal, including man, in need thereof comprising administration to said mammal of a therapeutically effective amount of an isolated protein according to the invention or a pharmaceutical composition according to the invention. In a preferred embodiment, the condition is Alzheimer's disease.

In one embodiment, the treatment is selected from the group consisting of preventive, palliative and curative treatment.

BRIEF DESCRIPTION OF THE DRAWINGS

FIG. 1 shows a schematic outline of Bri2 (SEQ ID NO: 1) processing.

FIG. 2 shows an alignment of human (SEQ ID NO:5), chimpanzee (SEQ ID NO:6), bovine (SEQ ID NO:7), swine (SEQ ID NO:8), murine (SEQ ID NO:9), and rat (SEQ ID NO:10) Bri2-Brichos amino acid sequences.

Figure 3:
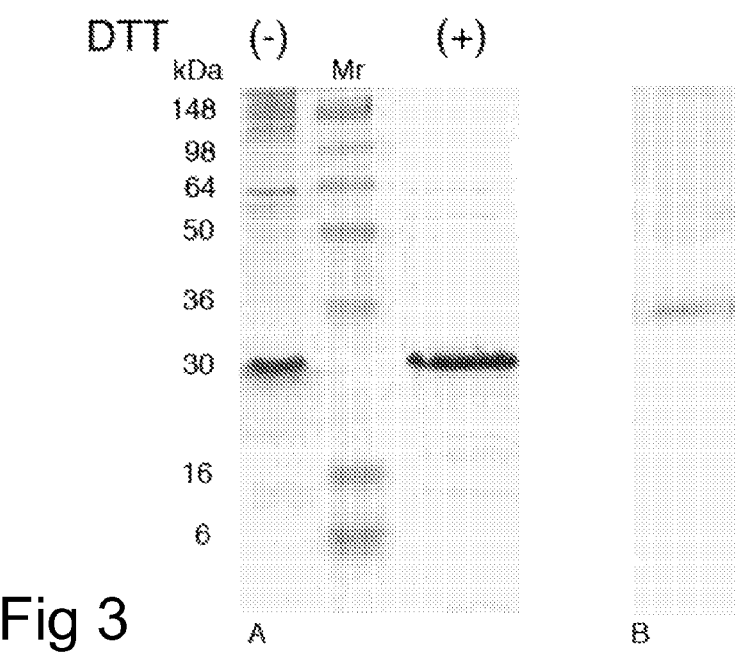
FIG. 3 shows SDS-PAGE (A) with (+) and without (−) reduction with dithiothreitol (DTT) and native gel electrophoresis (B) of recombinantly expressed Bri2(90-236) (SEQ ID NO: 2).

| List of appended sequences | |
|---|---|
| SEQ ID NO: 1 | human Bri2 |
| SEQ ID NO: 2 | human Bri2(90-236) |
| SEQ ID NO: 3 | human Bri2(1-89) |
| SEQ ID NO: 4 | human ABri23 [Bri2(244-266)] |
| SEQ ID NO: 5 | human Bri2$_{Brichos}$ [Bri2(137-231)] |
| SEQ ID NO: 6 | chimpanzee Bri2$_{Brichos}$ |
| SEQ ID NO: 7 | bovine Bri2$_{Brichos}$ |
| SEQ ID NO: 8 | pig Bri2$_{Brichos}$ |
| SEQ ID NO: 9 | mouse Bri2$_{Brichos}$ |
| SEQ ID NO: 10 | rat Bri2$_{Brichos}$ |
| SEQ ID NO: 11 | human $A\beta_{1-40}$ peptide |
| SEQ ID NO: 12 | human $A\beta_{1-42}$ peptide |
| SEQ ID NO: 13 | forward PCR primer |
| SEQ ID NO: 14 | reverse PCR primer |
| SEQ ID NO: 15 | synthetic peptide |

DETAILED DESCRIPTION OF THE INVENTION

Bri2 (SEQ ID NO: 1), also referred to as integral membrane protein 2B (ITM2B), contains an evolutionary conserved Brichos domain spanning residues 137-231 (SEQ ID NO: 5). Brichos domains are found in more than 10 different protein families that are functionally unrelated and expressed in different tissues. The name Brichos refers to identification of the domain in Bri, chondromodulin-1 related to chondrosarcoma and in lung surfactant protein C precursor (proSP-C) involved in respiratory disease. All of the so far identified Brichos-containing proteins are type II membrane proteins, and the Brichos domain is located in the C-terminal, ER lumenal region.

It has surprisingly been found that proteins comprising the Brichos domain of a mammalian Bri2 (ITM2B) and structurally similar proteins have the capacity to decrease amyloid fibril formation and aggregation of Aβ-peptide and ABri/ADan peptides.

The present invention provides an isolated protein that is useful as a medicament. The isolated protein is useful in treatment of a condition selected from the group consisting of Alzheimer's disease, familial Danish dementia and familial British dementia in a mammal, including man. In a preferred embodiment, the isolated protein is useful in treatment of Alzheimer's disease. The treatment may be a preventive, palliative or a curative treatment.

According to a first aspect, the present invention provides an isolated protein selected from the group of proteins consisting of residues 90-236 of Bri2 from human (SEQ ID NO: 2) and the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10). In certain embodiments, the isolated protein is selected from the group of proteins consisting of residues 90-236 of Bri2 from human (SEQ ID NO: 2); and the Brichos domain of Bri2 from human (SEQ ID NO: 5). In specific embodiments, the isolated protein is consisting of residues 90-236 of Bri2 from human (SEQ ID NO: 2) or the Brichos domain of Bri2 from human (SEQ ID NO: 5).

The present invention provides according to another aspect an isolated protein selected from the group consisting of proteins comprising an amino acid sequence having at least 70% identity to residues 90-236 of Bri2 from human (SEQ ID NO: 2); and proteins comprising an amino acid sequence having at least 70% identity to any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10).

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfil, instead of the specified percentage of identity, the corresponding percentage of similarity. Other alternative embodiments fulfil the specified percentage of identity as well as another, higher percentage of similarity, selected from the group of preferred percentages of identity for each sequence. For example, the isolated protein sequence may be 70% similar to another protein sequence; or it may be 70% identical to another sequence; or it may be 70% identical and furthermore 90% similar to another sequence.

For avoidance of doubt, the amino acid sequence having at least the given identity to residues 90-236 of Bri2 from human or any one of the Brichos domains of Bri2 consists of more than or equal to 70, such as more than or equal to 80, such as more than or equal to 90 amino acid residues. A preferable size range is 70-100 amino acid residues, such as 80-100 amino acid residues, e.g. 90-100 amino acid residues.

It is noted that the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10) is highly conserved, see alignment in FIG. 2. Without desiring to be bound to any specific theory, it is contemplated that the Brichos domain harbours the desired activity with respect to the Aβ and ABri/ADan peptides. It is preferred that the isolated protein according to the invention is selected from the group consisting of proteins comprising an amino acid sequence having at least 80%, preferably at least 90%, such as at least 95%, identity to any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10). In a preferred embodiment, the isolated protein according to the invention contains all amino acid residues that are conserved in the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10), i.e. all amino acid residues of SEQ ID NO: 5 except for residues 42, 76 and 82 (corresponding to residues 178, 212 and 218 in full-length Bri2, SEQ ID NO: 1). In specific embodiments, the isolated protein according to the invention is selected from the group consisting of proteins comprising any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10), i.e. it contains one of these Brichos domains, preferably the human Brichos domain (SEQ ID NO: 5).

In contrast to previous teachings, the isolated protein according to the invention is not comprising an amino acid sequence having at least 70% identity to residues 1-89 of Bri2 from human (SEQ ID NO: 3). In certain embodiments, the isolated protein according to the invention is not comprising an amino acid sequence having at least 50% identity to residues 1-89 of Bri2 from human (SEQ ID NO: 3). This implies that the isolated protein according to the invention contains a core amino acid sequence which displays a high similarity or identity to residues 90-236 of Bri2 from human (SEQ ID NO: 2) and/or a mammalian Brichos domain of Bri2 from (SEQ ID NOS: 5-10) and optionally one or more other amino acid sequences, which other amino acid sequences may not display a high similarity or identity to residues 1-89 of Bri2 from human (SEQ ID NO: 3).

For avoidance of doubt, amino acid sequences that are shorter than 10 amino acid residues are not considered relevant in the context of being excluded from the isolated protein according to the invention. Thus, the isolated protein according to the invention is not comprising an amino acid sequence that consists of more than or equal to 10 amino acid residues having at least the given identity to residues 1-89 of Bri2 from human (SEQ ID NO: 3).

Furthermore, the isolated protein according to the invention is not comprising an amino acid sequence having at least 70% identity to residues 244-266 of Bri2 from human, i.e. human ABri23 (SEQ ID NO: 4). In certain embodiments, the isolated protein according to the invention is not comprising an amino acid sequence having at least 50% identity to residues human ABri23 (SEQ ID NO: 4). As set out above, this implies that the isolated protein according to the invention contains a core amino acid sequence which displays a high similarity or identity to residues 90-236 of Bri2 from human (SEQ ID NO: 2) and/or a mammalian Brichos domain of Bri2 from (SEQ ID NOS: 5-10) and optionally one or more other amino acid sequences, which other amino acid sequences may not display a high similarity or identity to human ABri23 (SEQ ID NO: 4).

For avoidance of doubt, amino acid sequences that are shorter than 10 amino acid residues are not considered relevant in the context of being excluded from the isolated protein according to the invention. Thus, the isolated protein according to the invention is not comprising an amino acid sequence that consists of more than or equal to 10 amino acid residues having at least the given identity to human ABri23 (SEQ ID NO: 4).

In preferred embodiment, the isolated protein for use according to the invention is selected from the group consisting of proteins comprising an amino acid sequence having at least 70% identity to residues 90-236 of Bri2 from human (SEQ ID NO: 2); and proteins comprising an amino acid sequence having at least 70% identity to the Brichos domain of Bri2 from human (SEQ ID NO: 5).

Proteins comprising a core amino acid sequence having one or more identities with Bri2 target sequences as set out above may further comprise additional amino acid sequences which do not interfere with the function of the core amino acid sequence, i.e. interaction with Aβ and ABri/ADan proteins. The additional amino acid sequences may be connected to the N-terminal of the core amino acid sequence, to the C-terminal of the core amino acid sequence, or both. It may also be connected via amino acid side chains, e.g. via a disulphide bond. The additional amino acid sequences may be essentially non-functional or may provide additional functionality to the resulting protein, e.g. solubility, stability or a desired affinity. Both the core amino acid sequence and any additional amino acid sequences may be chemically modified, including post-translational chemical modifications.

In one embodiment, the isolated protein according to the invention is selected from the group of proteins consisting of an amino acid sequence having the identities set out above. That is, the isolated protein consists of the desired core amino acid sequence having one or more identities with Bri2 target sequences as set out above. The core amino acid sequence may be chemically modified, including post-translational chemical modifications.

In certain embodiments, the isolated protein according to the present invention consists of less than or equal to 500, such as less than or equal to 250, such as less than or equal to 200, such as less than or equal to 150 or even 100 amino acid residues. In certain embodiments, the isolated protein according to the present invention consists of more than or equal to 80, such as more than or equal to 90, such as more than or equal to 100 amino acid residues. A preferable size range is 80-200 amino acid residues, such as 90-150 amino acid residues, e.g. 90-100 amino acid residues.

It is experimentally shown herein that recombinant human Bri2(90-236) binds to ABri23. Which region of Bri2(90-236) that binds to the ABri23 peptide is not known. Without desiring to be bound to any specific theory, it is contemplated that it is the Brichos domain in Bri2, which is encompassed by Bri2(90-236), that mediates binding to ABri23. It is interesting to note that ABri23 has a high β-strand propensity. The Brichos domain may bind to peptide segments with high β-strand propensities, since all but one of the known Brichos domains are followed by a C-terminal peptide segment with high β-strand propensity. Binding of the uncleaved region corresponding to ABri23 to the Brichos domain in full-length Bri2 likely facilitates formation of the disulphide bridge between the two Cys in ABri23, compared to formation of the disulfides in free ABri23. If so, the Bri2 Brichos domain works as a chaperone that promotes correct folding of another part of the same pro-protein. The substrate specificity of Bri2(90-236) is unique in that it does not bind to any of the tripeptides that are exclusively composed of hydrophobic residues under gas phase conditions. It is interesting to note that the three long peptides that Bri2(90-136) binds to have certain motifs in common, see Table 1. Both ABri23 and $Aβ_{1-40}$ contain internal segments that resemble the KFFEYNGKKFFE (SEQ ID NO: 15) segments by having hydrophobic residues flanked by charged residues.

TABLE 1

Amino acid sequences of peptides found to bind recombinant human Bri2(90-236) (SEQ ID NO: 2). Side-chain charges are indicated above the respective sequence and nonpolar residues are underlined.

| | |
|---|---|
| $A\beta_{1-40}$ (SEQ ID NO: 11) | `- - ++-  - ++ +     --   +`<br>DAEFRHDSGYEVHHQKLVFFAEDVGSNKGAIIGLMVGGVV |
| ABri23 (SEQ ID NO: 4) | `      -     ++ - +   -`<br>EASNCFAIRHFENKFAVETLICS |
| SEQ ID NO: 15 | `+ -   ++ -`<br>KFFEYNGKKFFE |

The ability of Bri2(90-236) to bind $A\beta_{1-40}$ is intriguing as Bri2 has been implicated in binding to $A\beta$ and in APP processing. As regards binding to $A\beta$, it was suggested that ABri23 as such can bind $A\beta$ and prevent its aggregation (Kim et al., J. Neurosci. 28: 6030-6036 (2008)). Using electrospray mass spectrometry, binding between ABri23 and $A\beta$ could not be detected, but Bri2(90-236) was unequivocally found to bind $A\beta_{1-40}$. Moreover, Bri2(90-236), even at substoichiometric amounts reduce aggregation and fibril formation of $A\beta_{1-40}$. It is noted that both Bri2 and $A\beta$ are expressed in nervous tissue, and it is possible that they interact in vivo.

Recently, it was found that Bri2 affects the proteolytic processing of APP into $A\beta$, but that Bri2 needs to be proteolytically processed itself before it can interfere with APP processing (Matsuda et al. Neurobiol Aging. (2009), doi: 10.1016/j.neurobiolaging.2009.08.005). The present results give a possible explanation to these findings. Both ABri23 and $A\beta_{1-40}$ binds to Bri2(90-236), but apparently ABri23 binds stronger. Without desiring to be bound to any specific scientific theory, we suggest that in Bri2 the ABri23 region binds to the Brichos domain and this blocks interactions between Bri2 and APP. Proteolytic release of the ABri23 peptide makes the Bri2 binding pocket vacant for binding to the $A\beta$ region of APP. Binding of Bri2 to the $A\beta$ region of APP will likely reduce its processing by secretases.

According to another aspect, the present invention provides a pharmaceutical composition comprising a therapeutically effective amount of an isolated protein according to the invention and a suitable pharmaceutical carrier therefor. The pharmaceutical composition is useful as a medicament, The pharmaceutical composition is useful in treatment of a condition selected from the group consisting of Alzheimer's disease, familial Danish dementia and familial British dementia in a mammal, including man. Specifically, the pharmaceutical composition is useful in treatment of Alzheimer's disease in a mammal, including man.

According to a related aspect, the present invention provides use of an isolated protein according to the invention for the manufacture of a medicament for the treatment of a condition selected from the group consisting of Alzheimer's disease, familial Danish dementia and familial British dementia in a mammal, including man. In a preferred embodiment, the condition is Alzheimer's disease.

The isolated protein according to the invention can be incorporated into pharmaceutical compositions. Such compositions typically include the isolated protein according to the invention and a suitable pharmaceutically acceptable carrier. As used herein, a "suitable pharmaceutical carrier" includes solvents, dispersion media, coatings, isotonic and absorption delaying agents, and the like, that are compatible with pharmaceutical administration. Supplementary active compounds can also be incorporated into the compositions.

A pharmaceutical composition is formulated to be compatible with its intended route of administration. Examples of routes of administration include parenteral (e.g. intravenous, intradermal, subcutaneous), oral, intranasal (e.g. inhalation), transdermal, transmucosal, intrathecal, intracerebral ventricular (e.g. using an Omaya reservoir-shunt with in-line filter that is surgically placed into the cisternal space), and rectal administration.

Potentially useful parenteral delivery systems for a composition include slow-dissolving polymer particles, implantable infusion systems, and liposomes. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Treatment of the conditions Alzheimer's disease, familial Danish dementia and familial British dementia may also be effected by direct delivery of the isolated protein according to the invention to the central nervous system, preferentially to the brain.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating on particles of the isolated protein according the invention (e.g. lecithin), by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents in the composition. Example of such agents include sugars, polyalcohols such as mannitol and sorbitol, and sodium chloride. Prolonged absorption of the injectable compositions can be brought about by including in the composition an agent which delays absorption, for example, aluminum monostearate or gelatin.

Sterile injectable solutions can be prepared by incorporating the isolated protein according to the invention in the required amount in an appropriate solvent with one or a combination of ingredients enumerated above, as required, followed by filtered sterilization. Generally, dispersions are prepared by incorporating the isolated protein according the invention into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the isolated protein according the invention plus any additional desired ingredient from a previously sterile-filtered solution thereof.

Oral compositions generally include an inert diluent or an edible carrier. For the purpose of oral therapeutic administration, the isolated protein according the invention can be incorporated with excipients and used in the form of tablets, troches, or capsules, e.g., gelatin capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g. a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the isolated protein according the invention is formulated into ointments, salves, gels, or creams as generally known in the art.

The isolated protein according the invention can also be prepared in the form of suppositories (e.g. with conventional suppository bases such as cocoa butter and other glycerides) or retention enemas for rectal delivery.

In one embodiment, the isolated protein according the invention is prepared with a carrier that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to cells specifically affected by Alzheimer's disease, familial Danish dementia or familial British dementia with monoclonal antibodies) can also be used as pharmaceutically acceptable carriers. These can be prepared according to methods known to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of the isolated protein according the invention calculated to produce the desired therapeutic effect in association with the required pharmaceutical carrier.

Toxicity and therapeutic effects of the isolated proteins according to the invention can be determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). Suitable animal models can be used such as those described for amyloidoses in Sturchler-Pierrat et al, Rev Neurosci, 10: 15-24, 1999; Seabrook et al, Neuropharmacol 38: 1-17, 1999; DeArmond et al, Brain Pathology 5: 77-89, 1995; Telling, Neuropathol Appl Neurobiol 26: 209-220, 2000; and Price et al, Science 282: 1079-1083, 1998.

The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to unaffected cells and thereby reduce side effects.

Data obtained from the cell culture assays and animal studies can be used in formulating a range of dosage for use in humans. The dosage of a compound lies preferably within a range of circulating concentrations that include the $ED_{50}$ with little or no toxicity.

The dosage may vary within this range depending upon the dosage form employed and the route of administration utilized. For any compound used in the method of the invention, the therapeutically effective dose can be estimated initially from cell culture assays in which, e.g. the rate of fibril formation or the rate of cell death is observed. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an isolated protein according to the invention (i.e., an effective dosage) ranges from about 0.1 to 100 mg/kg body weight, more preferably about 1 to 100 mg/kg body weight, and even more preferably about 1 to 50 mg/kg body weight. The compound can be administered over an extended period of time to the subject, e.g., over the subject's lifetime. A dosage of 1 mg/kg to 100 mg/kg is usually appropriate, such as is the case for antibodies designated to act in the brain.

In some cases the compound can be administered once per week for between about 1 to 10 weeks, preferably between 2 to 8 weeks, more preferably between about 3 to 7 weeks, and even more preferably for about 4, 5, or 6 weeks. The compound can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

Recombinant isolated proteins according to the invention, including human Bri2(90-236) and the Brichos domain of Bri2, for administration to mice expressing the human APP or to humans can be prepared in several ways. The recombinant proteins can be purified as described in Example 1. For increasing the likelihood of the proteins to pass the blood brain barrier (BBB) several methods are envisioned.

A couple of main strategies have emerged for drug passage through the BBB. They make use of endogenous transport systems, either by receptor-mediated transcytosis or by use of specific receptors, e.g. for glucose, amino acids or peptides. Peptides seem particularly attractive as vectors for carrying diverse cargos across the BBB. A number of different peptides have been shown to trigger endocytosis (typically by the LDL-receptor) and to be able to deliver a cargo across the BBB. Some of these peptides are amphiphilic positively charged cell penetrating peptides (CPPs, e.g. penetratin, ApoE derived peptide and other) but these can also be highly toxic at higher doses. Others like the synB family are also positively charged but without the hydrophobic part. A drawback of many of the endocytosis triggering peptides is that they, in order to be efficient, need be relatively large in order to form stable α-helices, which seems to correlate with efficient uptake. The advantage with delivery by transcytosis is that the cargo can be quite substantial and quite variable. A path where specific endogenous peptides, that have been shown to cross the BBB by a saturable transport system, would act as vectors for drug delivery is also a viable alternative. Several relatively short peptides of this kind, like MIF-1 (Pro-Leu-Gly, derived from oxytocin) and Peptide T (8 residues, derived from the HIV envelope) have been shown be efficiently transported across the BBB. See e.g. de Boer A G and Gaillard P J, Clin Pharmacokinet. 46:553-76, 2007; de Boer A G and Gaillard P J, Annu Rev Pharmacol Toxicol. 47:323-55, 2007; Pardridge W M, Drug Discov Today. 12:54-61, 2007, for descriptions of methods for delivery across the BBB. In the present case, it is envisioned that said peptides or proteins can be mixed with human Bri2(90-236) or the Brichos domain of Bri2, or alternatively they can be expressed covalently linked to human Bri2(90-236) or the Brichos domain of Bri2.

In other formulations, human Bri2(90-236) or the Brichos domain of Bri2 can be linked to nanoparticles for delivery across the BBB (Lockman P R et al., Drug Dev Ind Pharm. 28:1-13, 2002; Tosi G et al., Expert Opin Drug Deliv. 5:155-74, 2008).

Modifications such as lipidation can also be used to stabilize proteins and to enhance uptake and tissue penetration (e.g., into the brain). A method for lipidation of antibodies is described by Cruikshank et al, J Acquired Immune Deficiency Syndromes Hum Retrovirol 14: 193, 1997.

When an isolated protein according to the invention is to be administered to an animal (e.g. a human) to treat Alzheimer's disease, familial Danish dementia or familial British dementia, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions of the invention can be included in a container, pack, or dispenser together with instructions for administration. For example, the instructions can include directions to use the composition to treat an individual having or at risk for Alzheimer's disease, familial Danish dementia or familial British dementia According to another aspect, the present invention provides a method of treating Alzheimer's disease, familial Danish dementia or familial British dementia, in a mammal, including man, in need thereof comprising administration to said mammal of a therapeutically effective amount of an isolated protein according to the invention or a pharmaceutical composition according to the invention.

In specific embodiments, the treatment may be a preventive treatment. In other specific embodiments, the treatment may be a palliative treatment. In certain specific embodiments, the treatment may be a curative treatment.

The present invention provides for both prophylactic and therapeutic methods of treating a subject at risk of (or susceptible to) Alzheimer's disease, familial Danish dementia or familial British dementia. As used herein, the term "treatment" is defined as the application or administration of an isolated protein according to the invention to a patient, or application or administration of an isolated protein according to the invention to an isolated tissue or cell line from a patient, who has Alzheimer's disease, familial Danish dementia or familial British dementia, a symptom of disease or a predisposition toward a disease, with the purpose to cure, heal, alleviate, relieve, alter, remedy, ameliorate, improve or affect the disease, the symptoms of disease or the predisposition toward disease.

In one aspect, the invention provides a method for preventing a disease or condition (i.e., decreasing the risk of contracting, or decreasing the rate at which symptoms appear that are associated with a disease or condition) associated with fibril formation caused by Aβ peptide and/or ABri/ADan peptide by administering to the subject an isolated protein according to the invention that reduces aggregation of the polypeptide. Subjects at risk for Alzheimer's disease, familial Danish dementia or familial British dementia can be identified by, for example, any or a combination of appropriate diagnostic or prognostic assays known in the art. Administration of a prophylactic agent can occur prior to the manifestation of symptoms characteristic of the disease, such that the disease is prevented or, alternatively, delayed in its progression.

The isolated protein according to the invention can be administered to a patient at therapeutically effective doses to prevent, treat or ameliorate disorders involving fibril formation associated with Alzheimer's disease, familial Danish dementia or familial British dementia. A therapeutically effective dose refers to that amount of the compound sufficient to result in amelioration of symptoms of the disorders. Toxicity and therapeutic efficacy of such compounds can be determined by standard pharmaceutical procedures as described above.

It is also contemplated that the protein according to the invention can be administrated by gene therapy, such as by using expression vectors, plasmids or viruses to transfect cells in the neural system, preferably brain, such that the isolated protein is expressed by these cells in the central neural system. This is useful for the treatment of Alzheimer's disease, familial Danish dementia or familial British dementia.

The present invention will now be further illustrated by the following non-limiting examples.

EXAMPLES

Example 1

Recombinant Bri2(90-236) Expression and Purification

The cDNA corresponding to human Bri2 residues 90-236 (SEQ ID NO: 2) was amplified from PCR ready human brain cDNA library (Ambion), using forward primer 5'-GGTGC-CATGGGAATA-3' (SEQ ID NO: 13) and reverse primer 5'-CTCTAGAGGATCCCT-3' (SEQ ID NO: 14) (both from DNA technology AIS, Aarhus, Danmark). After digestion with BamH1 and Nco1, the amplified cDNA was subcloned into pET-32c vector (Novagen, Madison, Wis.), coding for $His_6$-, thioredoxin-, and S-tags preceding the insert, for increasing solubility and facilitating purification by affinity chromatography. After transformation into *E. coli* strain Origami(DE3)pLysS (Novagen, Madison, Wis.), selected bacterial colonies were cultured in Luria-Bertani (LB) medium with 100 μg/ml ampicillin at 30° C. for 16 hours until $OD_{600}$ reached 0.8. Protein expression was then induced by adding 0.25 mM isopropylthiogalactoside (IPTG), and cells were left for 6 h at 25° C. Cells were then harvested by centrifugation at 5000-6000 g for 20 min, resuspended in 20 mM sodium phosphate buffer, pH 7.0, containing 5 mM imidazole and stored at −80° C. until use.

Bacterial pellets were sonicated and then centrifuged at 6000 g for 30 min. The supernatant was filtered through 0.2 μm filter, applied to a 3 ml Nickel-nitrilotriacetic acid-agarose (Qiagen Ltd., West Sussex, UK) column equilibrated in 20 mM sodium phosphate buffer, pH 7.0, containing 5 mM imidazole. The column was washed with 5-50 mM imidazole, until the OD at 280 nm of the eluate was near zero. The fusion protein was then eluted with 100 mM imidazole in the same buffer, collected and dialyzed against 20 mM sodium phosphate buffer, pH 7.0. $His_6$- and thioredoxin tags were removed by cleavage with thrombin (from bovine plasma, Merck, Germany), at an enzyme/protein weight ratio of 0.002, incubated for 2 h at 20° C., and removed by another passage over the Ni-column. The eluted target protein was analyzed by SDS-PAGE, native gel electrophoresis, as well as circular dichroism (CD) spectroscopy. Far-UV CD spectroscopy was performed using a J-820 spectrophotometer (Jasco, Japan), protein concentration of 25 μM in 2 mM phosphate buffer, pH 7.0, and an optical path length of 0.1 cm.

A fragment corresponding to Bri2 positions 90-236 (SEQ ID NO: 2) was expressed as a soluble fusion protein together with hexahistidine, thioredoxin and S-tags in *E. coli*, and purified by immobilized metal affinity chromatography. After cleavage with thrombin and removal of affinity and solubility tags, about 30 mg S-tagged Bri2(90-236) with a purity of >90% was obtained per liter bacterial culture, as analyzed by SDS and native gel electrophoresis (FIG. 3).

Figure 4:
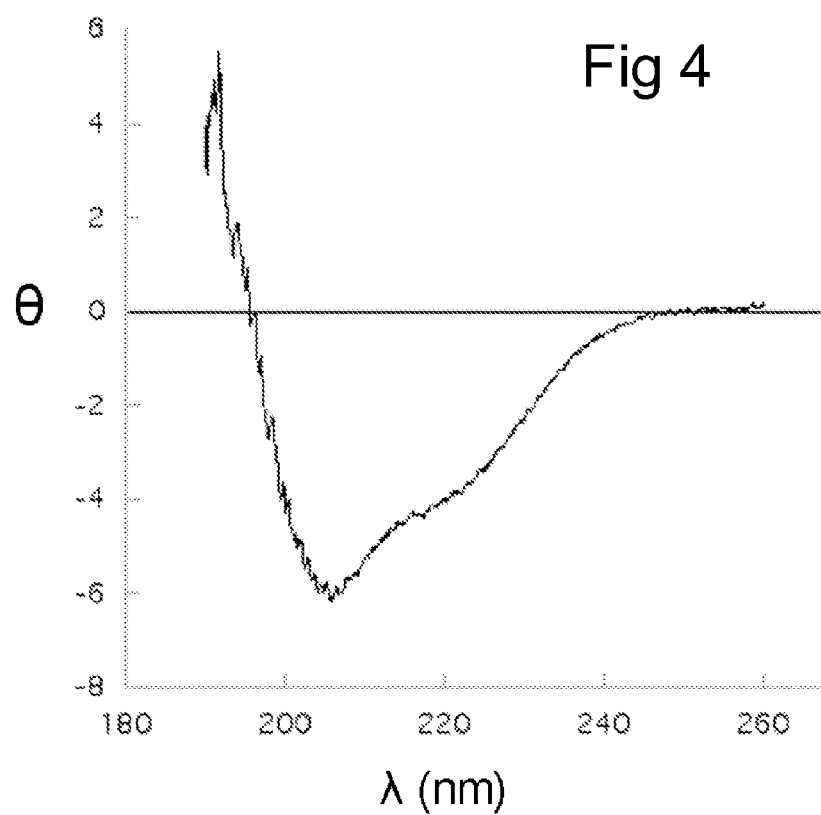
FIG. 4 shows a CD spectrum of recombinant Bri2(90-236) (SEQ ID NO: 2).

FIG. 3 shows SDS-PAGE (A) with (+) and without (−) reduction with dithiothreitol (DTT) and native gel electrophoresis (B) of recombinantly expressed Bri2(90-236). As shown in FIG. 3, analysis of unreduced Bri2(90-236) indicates that a major fraction of the protein is monomeric, and the multimeric forms can be removed by reduction (+). This suggests that the two Cys residues in Bri2(90-236) preferentially form intramolecular disulfide bonds. The CD spectrum of Bri2(90-236) (FIG. 4) indicates that the protein is folded into a mainly α-helical/disordered structure. This is in reasonable agreement with the predicted secondary structure of the same region, which suggests mainly unordered structure and about equal contents of α-helix and β-sheet. In FIG. 4, the mean molar residual ellipticity (θ) is expressed as $kdeg \times cm^2/dmol$.

Example 2

Binding of Peptides to Bri2(90-236) Investigated by ESI-MS

Prior to electrospray ionization mass spectrometry (ESI-MS), purified Bri2(90-236) (SEQ ID NO: 2) was rebuffered into 10 mM ammonium acetate, pH 7.0, using spin columns with a 3 kDa cut-off limit (Nanosep, Pall Corp., East Hills, N.Y., USA). Protein and peptides were mixed at 22° C. directly before analysis at a final protein concentration of 20 μM and a final peptide concentration of 50 μM. Data was acquired using a QTOF Ultima API mass spectrometer (Waters, Milford, Mass., USA) equipped with a Z-spray source operated in the positive-ion mode. Samples were introduced via nano-electrospray using metal-plated borosilicate glass capillary needles (Proxeon, Denmark). The source temperature was 80° C., the capillary voltage 1.7 kV, and the cone and RF lens 1 potentials were 100 and 38 V, respectively. The mass spectrometer was operated in single-reflector mode at a resolution of 10 000 (full width half maximum definition), and the mass scale was calibrated using myoglobin. Scans were acquired at a rate of 1 scan per 2 sec between 500 and 4000 m/z. The collision gas was argon at $5.2 \times 10^{-5}$ mbar. Mass spectra were smoothed using the Waters MassLynx software.

All peptides, with the exception of KFFEYNGKKFFE (SEQ ID NO: 15), ABri23 (SEQ ID NO: 4) and $A\beta_{1-40}$ (SEQ ID NO: 11), were purchased from Thermo Electron (Darmstadt, Germany). KFFEYNGKKFFE was purchased from Interactiva (Ulm, Germany) and $A\beta_{1-40}$ and disulfide-linked ABri23 were from Bachem (Bubendorf, Switzerland).

Peptides, except for KFFEYNGKKFFE, ABri23 and $A\beta_{1-40}$, were acetylated at the N-terminus and amidated at the C-terminus. The compositions of all peptides were verified by ESI-MS and amino acid analysis. Peptide YYY was dissolved to a final concentration of 10 mM in 30% acetonitrile. VVV, FFF and LLL were dissolved in 50% isopropanol to a final concentration of 10 mM. KKK, GGG and AAA were dissolved in water to a final concentration of 10 mM, while KFFEYNGKKFFE and ABri23 were dissolved in water to final concentrations of 5.6 mM and 1 mM, respectively. All peptide samples were stored at −20° C., except for $A\beta_{1-40}$ which was dissolved to a final concentration of 1 mM in water directly prior to analysis.

ESI-MS binding experiments were conducted to investigate whether Bri2(90-236) can bind the peptides ABri23 and $A\beta_{1-40}$. For this purpose, Bri2(90-236) was mixed with ABri23, $A\beta_{1-40}$, or an equimolar mixture of ABri23 and $A\beta_{1-40}$, to a final concentration of 20 μM Bri2(90-236) and 50 μM of each peptide, and analyzed by ESI-MS. Mass spectra were recorded to investigate the presence and stoichiometry of protein-peptide complexes in the gas phase.

Figure 5:
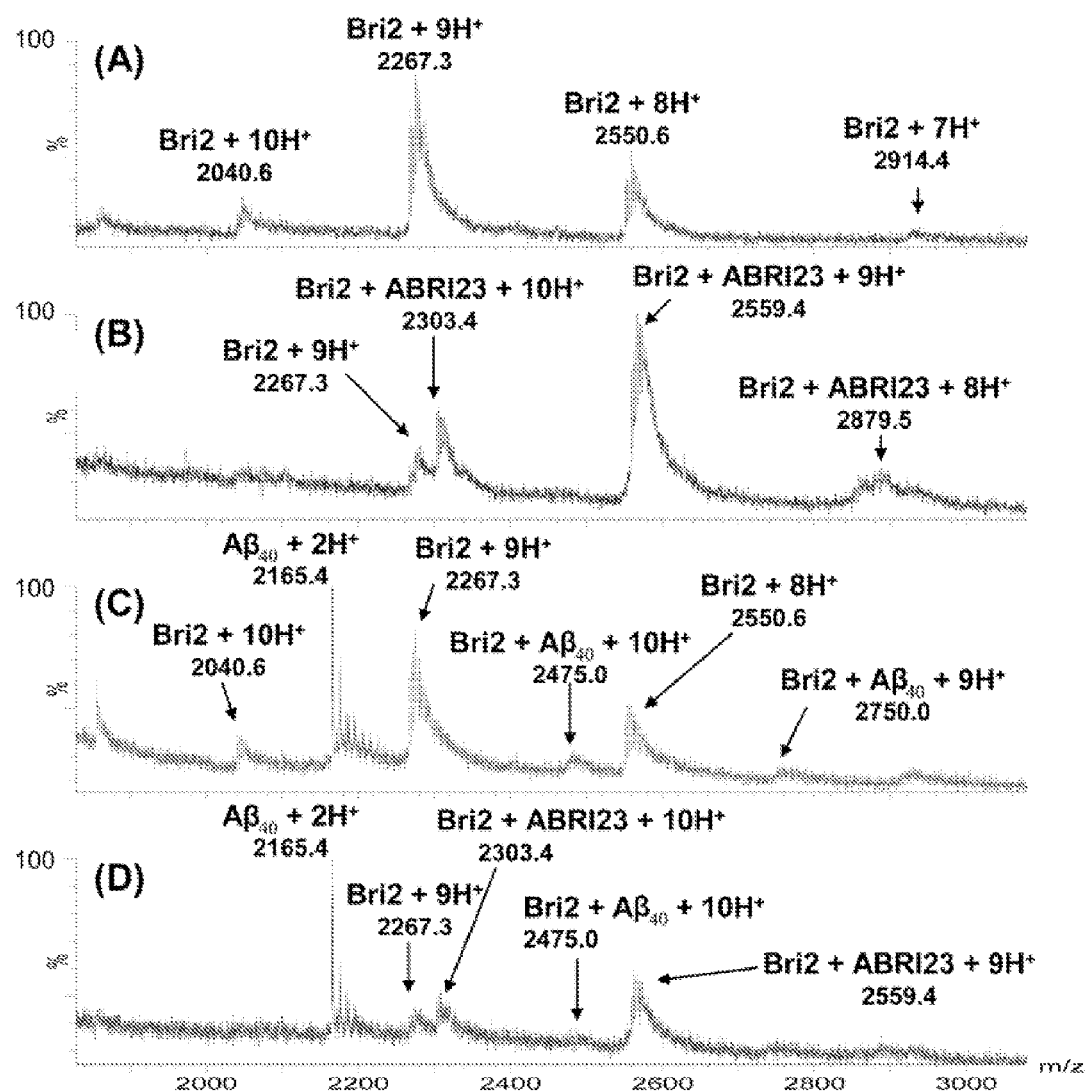
FIG. 5 shows ESI-MS spectra of recombinant Bri2(90-236) (SEQ ID NO: 2) alone (A) and in the presence of ABri23 (SEQ ID NO: 4) (B), $A\beta_{1-40}$ (SEQ ID NO: 11) (C), and both ABri23 and $A\beta_{1-40}$ (D).

ESI-MS spectra of 20 μM recombinant Bri2(90-236) without peptide showed a series of peaks at m/z 2040.6, 2267.3, and 2550.6, representing the charge states $[M+10H]^{10+}$, $[M+9H]^{9+}$ and $[M+8H]^{8+}$ of the monomeric form of the protein with a molecular mass of 20397±2 Da (FIG. 5A).

Addition of a 2.5-fold molar excess of oxidized ABri23 (50 μM; theoretical mass: 2627.9 Da) to the Bri2(90-236) protein (20 μM) led to a near-complete shift of the $[M+10H]^{10+}$ and

[M+9H]$^{9+}$ Bri2(90-236) peaks to m/z 2303.4 and m/z 2559.4, corresponding to the mass of a 1:1 Bri2(90-236)/ABri23 complex, with a calculated monoisotopic mass of 23028.4 Da, divided by the 10 or 9 charges, respectively (FIG. 5B). Heteromers of recombinant Bri2(90-236) and ABri23 were observed with 10, 9 and 8 charges. Only small amounts of free recombinant Bri2(90-236) were observed for the corresponding [M+10H]$^{10+}$, [M+9H]$^{9+}$ and [M+8H]$^{8+}$ charge states, indicating a near-complete saturation of recombinant Bri2 (90-236) with ABri23 under ESI-MS conditions. The correct assignment of a Bri2(90-236)/ABri23 complex was verified by collision-induced dissociation of the m/z 2303.4 ion, which at a collision voltage above 40 eV was found to dissociate into Bri2(90-236) with 8, 9 and 10 charges and ABri23 with 1 or 2 charges (data not shown).

Similarly, addition of a 2.5 fold excess of freshly dissolved Aβ$_{1-40}$ (50 μM; theoretical mass 4328.8 Da) to the Bri2(90-236) protein (20 μM) led to the appearance of peaks at m/z 2750.0 and m/z 2475.0, corresponding to 1:1 complexes of Bri2(90-236) and Aβ$_{1-40}$ with 9 and 10 charges, respectively (FIG. 5C). Only small amounts of recombinant Bri2(90-236)/Aβ$_{1-40}$ complexes were observed for the [M+10H]$^{10+}$ and [M+9H]$^{9+}$ charge states. As for the Bri2(90-236)/ABri23 complex, collision-induced dissociation of the m/z 2475.0 ion led to the dissociation of the complex into Bri2(90-236) with 9 and 10 charges, and Aβ$_{1-40}$ with 3 charges (data not shown).

While the addition of ABri23 led to a near-complete saturation of Bri2(90-236) with ABri23, addition of Aβ$_{1-40}$ at the same protein/peptide ratio resulted in the formation of only a small fraction of Bri2(90-236) in complex with Aβ$_{1-40}$ (FIGS. 5B and C). Competition experiments with both peptides present at equimolar amounts supported this observation, with visible formation of Bri2(90-236)/ABri23 complexes, but only minor signals corresponding to a Bri2(90-236)/Aβ$_{1-40}$ complex (FIG. 5D). FIG. 5D shows an ESI-MS spectrum of 20 μM recombinant Bri2(90-236) in the presence of 50 μM Aβ$_{1-40}$ and ABri23. A small peak corresponding to recombinant Bri2(90-236) in complex with Aβ$_{1-40}$ can be observed for the [M+10H]$^{10+}$ charge state, even though nearly all detectable recombinant Bri2(90-236) is complexed with ABri23. This suggests that Bri2(90-236) preferentially binds ABri23, or that a Bri2(90-236)/ABri23 complex is more stable under the conditions used for mass spectrometry.

Figure 6:
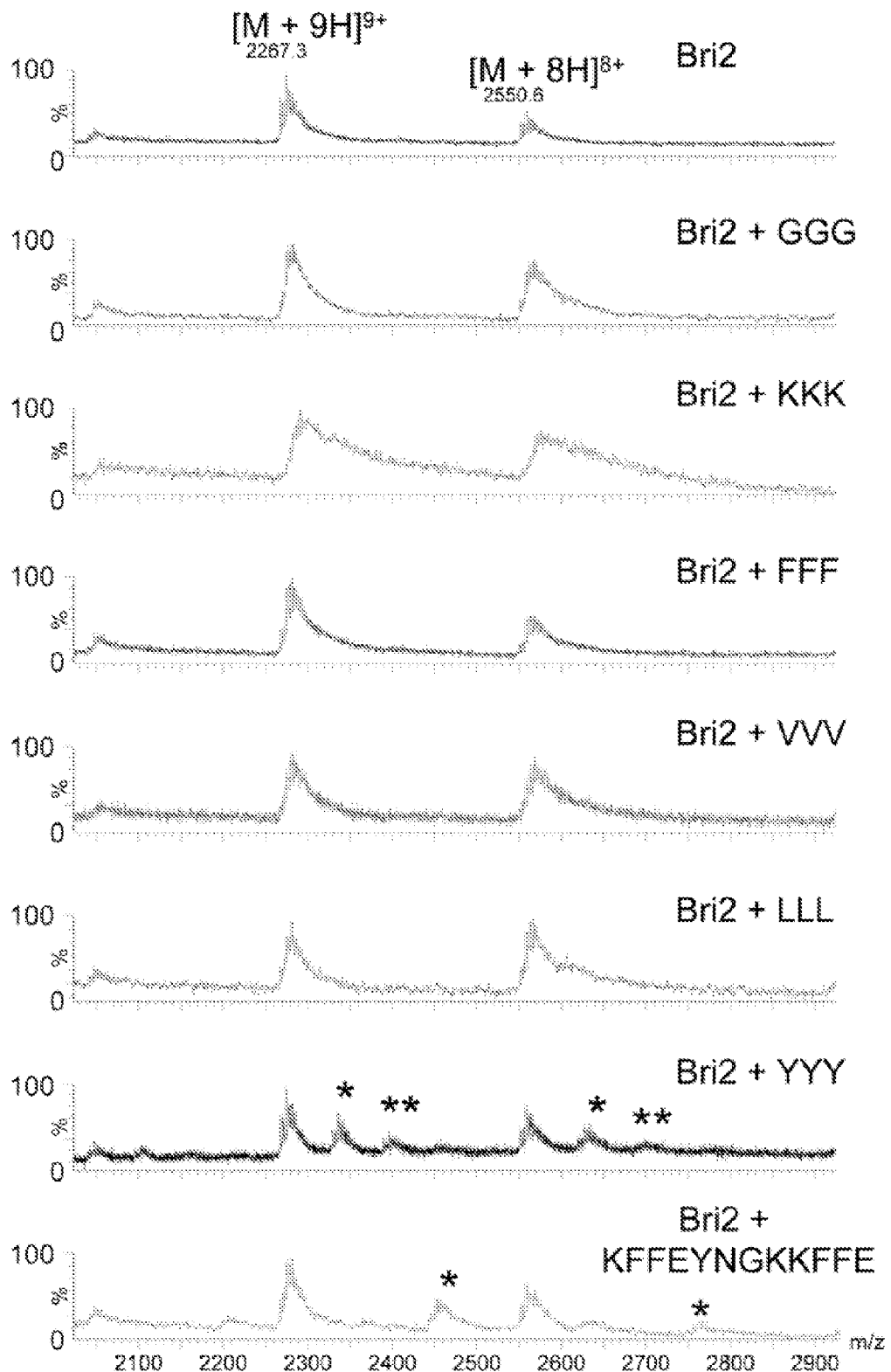
FIG. 6 shows ESI-MS spectra of recombinant Bri2(90-236) (SEQ ID NO: 2) in the presence of various peptides, including SEQ ID NO: 15.

To further investigate the substrate specificity of Bri2(90-236), homotripeptides with aromatic (YYY, FFF), hydrophobic (VVV, LLL), charged (KKK) or small uncharged (AAA, GGG) side-chains, were employed to study binding, under maintained water solubility. FIG. 6 shows ESI-MS spectra of 20 μM recombinant Bri2(90-236) in the presence of 50 μM of different peptides. The peptide sequences are denoted in each spectrum. Symbols * and ** indicate peaks corresponding to recombinant Bri2(90-236) with one or two peptide ligands, respectively. No interactions were observed for FFF, VVV, LLL, KKK, AAA, or GGG at a peptide/protein ratio of 2.5. Only YYY and KFFEYNGKKFFE were found to form complexes with recombinant Bri2(90-236) under ESI-MS conditions. In the case of YYY, peaks corresponding to complexes of Bri2(90-236) with one or two YYY molecules were observed (FIG. 6), indicating that Bri2(90-236) is capable of interacting with this tripeptide in the gas phase. Bri2(90-236) also binds the peptide KFFEYNGKKFFE (FIG. 6).

Example 3

Bri2(90-233) Effects on Aβ$_{1-40}$ Aggregation and Fibril Formation

25 μM of Aβ$_{1-40}$ (SEQ ID NO: 11) was incubated with or without recombinant Bri2(90-236) (SEQ ID NO: 2) in 20 mM phosphate buffer, pH 7.0 at 37° C. for 48 h, with 200 rpm agitation, at Aβ/Bri2(90-236) molar ratios of 1:1, 2:1, or 10:1. Aβ$_{1-40}$ was dissolved in 100% DMSO to 250 μM stock solution, which was diluted to working concentrations. For Thioflavin T (ThT) fluorescence measurements, 10 μl aliquots were removed at different time points, 10 μM ThT (Aldrich) added, and fluorescence was measured with a Far-Cyte fluorescence plate reader (GE Healthcare), emission wavelength is 480 nm, excitation wavelength 440 nm. Measurements of ThT were done in duplicates.

For analysis of soluble Aβ$_{1-40}$ and ultrastructure of Aβ aggregates, aliquots were removed and centrifuged at 3300 g for 9 min. The supernatant was analyzed by SDS-PAGE and pellets were resuspended in 200 μl distilled water, 2 μl of the resuspension was added onto 200 mesh copper electron microscopy grids, stained with 2% uranyl acetate for 30 s, then left to dry at 20° C. A Hitachi H 7100 microscope operated at 75 kV was used for examination and photographing.

Figure 7:
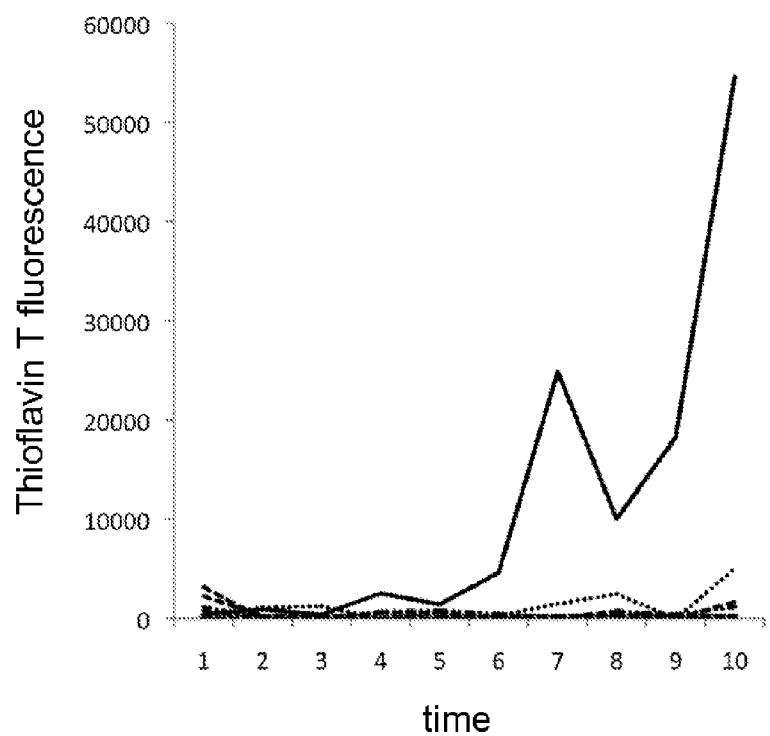
FIG. 7 shows Thioflavin T (ThT) fluorescence of $A\beta_{1-40}$ (SEQ ID NO: 11) alone (solid line) and mixed with recombinant Bri2(90-236) (SEQ ID NO: 2) at different ratios (dotted and dashed lines).

In the absence of Bri2(90-236), Aβ$_{1-40}$ starts to form aggregates rich in β-sheet after 7 h, as judged by ThT fluorescence. However, when incubated together with Bri2(90-236), independent of Aβ$_{1-40}$/Bri2(90-236) ratio, no ThT positive aggregates were found within the 24 h period studied. FIG. 7 displays ThT fluorescence of Aβ$_{1-40}$ alone (solid line) and mixed with recombinant Bri2(90-236) at 1:1, 2:1, and 10:1 ratios (dotted and dashed lines).

Figure 8:
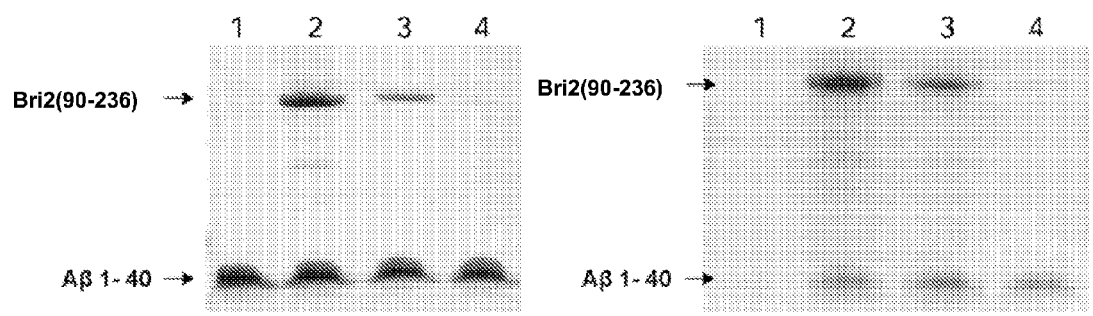
FIG. 8 shows SDS-PAGE of supernatants obtained at different time points of $A\beta_{1-40}$ (SEQ ID NO: 11) alone (lane 1) and mixed with recombinant Bri2(90-236) (SEQ ID NO: 2) at different ratios (lanes 2-4).

Likewise, co-incubation with Bri2(90-236) results in Aβ$_{1-40}$ staying in solution even after 3 weeks incubation, as judged by SDS-PAGE of supernatants obtained by centrifugation at 3300 g. FIG. 8 shows SDS-PAGE of supernatants obtained at time 0 (left gel) and after 5 days incubation at 37° C. (right gel) of 25 μM Aβ$_{1-40}$ alone (lane 1), or mixed with recombinant Bri2(90-236) at 1:1, 2:1, and 10:1 ratios (lanes 2-4).

Figure 9:
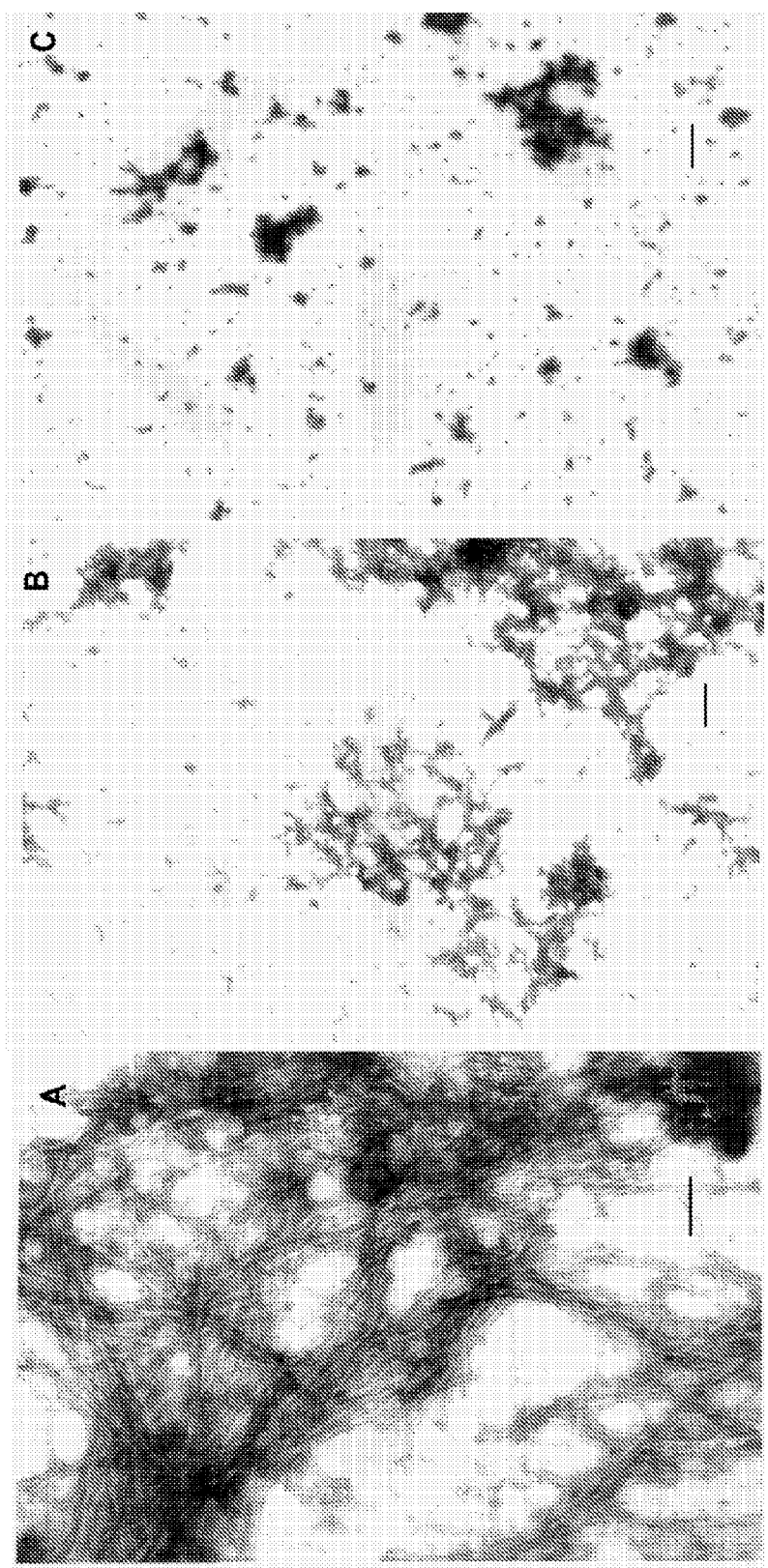
FIG. 9 shows the electromicroscopic appearance of $A\beta_{1-40}$ (SEQ ID NO: 11) (A), recombinant Bri2(90-236) (SEQ ID NO: 2) (C) or a combination of $A\beta_{1-40}$ and Bri2(90-236) at 1:1 molar ratio for 5 days (B).

Electron microscopy of pellets formed after 5 days showed that Aβ$_{1-40}$ formed amyloid-like fibrils, and that co-incubation with Bri2(90-236) results in lower amounts of fibrils. FIG. 9 shows the appearance of Aβ$_{1-40}$ incubated alone (A) or together with recombinant Bri2(90-236) at 1:1 molar ratio for 5 days (B). Also recombinant Bri2(90-236) incubated alone is shown (C). Scale bars represent 100 μm in A and 50 μm in B and C.

Example 4

Bri2(90-236) Effects on Aβ$_{1-40}$ and Aβ$_{1-42}$ Fibril Formation

Aβ$_{1-40}$ (SEQ ID NO: 11) and Aβ$_{1-42}$ (SEQ ID NO: 12) were expressed in *E. coli* from synthetic genes and purified in batch format using ion exchange and size exclusion steps as described in Walsh et al., FEBS J. 2009, 276, 1266-1281, which results in highly pure monomeric peptide. Purified peptide was divided into 20-30 identical aliquots and frozen. Monomer was then isolated by gel filtration of an aliquot of purified peptide just prior to setting up each of the experiments listed below to remove traces of aggregate formed during freezing and thawing and to exchange buffer to the one used in the respective experiment. Monomer was collected in low-bind Ep-tubes (Axygene) on ice, and the concentration was determined by absorbance or amino acid analysis after acid hydrolysis. The monomer was used as is or diluted to the desired concentration for the respective experiment. Bri2(90-236) (SEQ ID NO: 2) was expressed and purified as described in Example 1.

Aggregation kinetics were studied by recording the Thioflavin T (ThT) fluorescence intensity as a function of time in a plate reader (FluoStar Omega from BMG Labtech, Offenberg, Germany). The fluorescence was recorded using bottom optics in half-area 96-well PEG-coated black polystyrene plates with clear bottom (Corning 3881) using 440 nm excitation filter and 480 nm emission filter. Aβ monomer was isolated by gel filtration as above in 20 mM Na-phosphate, 200 µM EDTA, 0.02% NaN$_3$ (at pH 7.4 in the case of Aβ$_{1-40}$ and at pH 8.0 for Aβ$_{1-42}$) and diluted to 6 or 8 µM in the case of Aβ$_{1-40}$ and 3 µM in the case of Aβ$_{1-42}$ in the same buffer and supplemented with 20 µM ThT from a 2 mM stock.

To each well in the 96-well plate was first added either 10 µl buffer (20 mM Tris/HCl pH 7.4) or 10 µl of Bri2(90-236) protein or control protein at ten times the desired final concentration in 20 mM Tris/HCl pH 7.4. To each well was then added 90 µl of the ice-cold Aβ monomer solution, and the plate was immediately placed in the plate reader at 37° C., with fluorescence read every 6 minutes with continuous shaking at 100 rpm between readings.

Aβ$_{1-40}$ was studied alone or with Bri2(90-236) at a concentration ranging from 60 nM to 6 µM. Aβ$_{1-42}$ was studied alone or with Bri2(90-236) at a concentration ranging from 20 nM to 6 µM.

Figure 10:
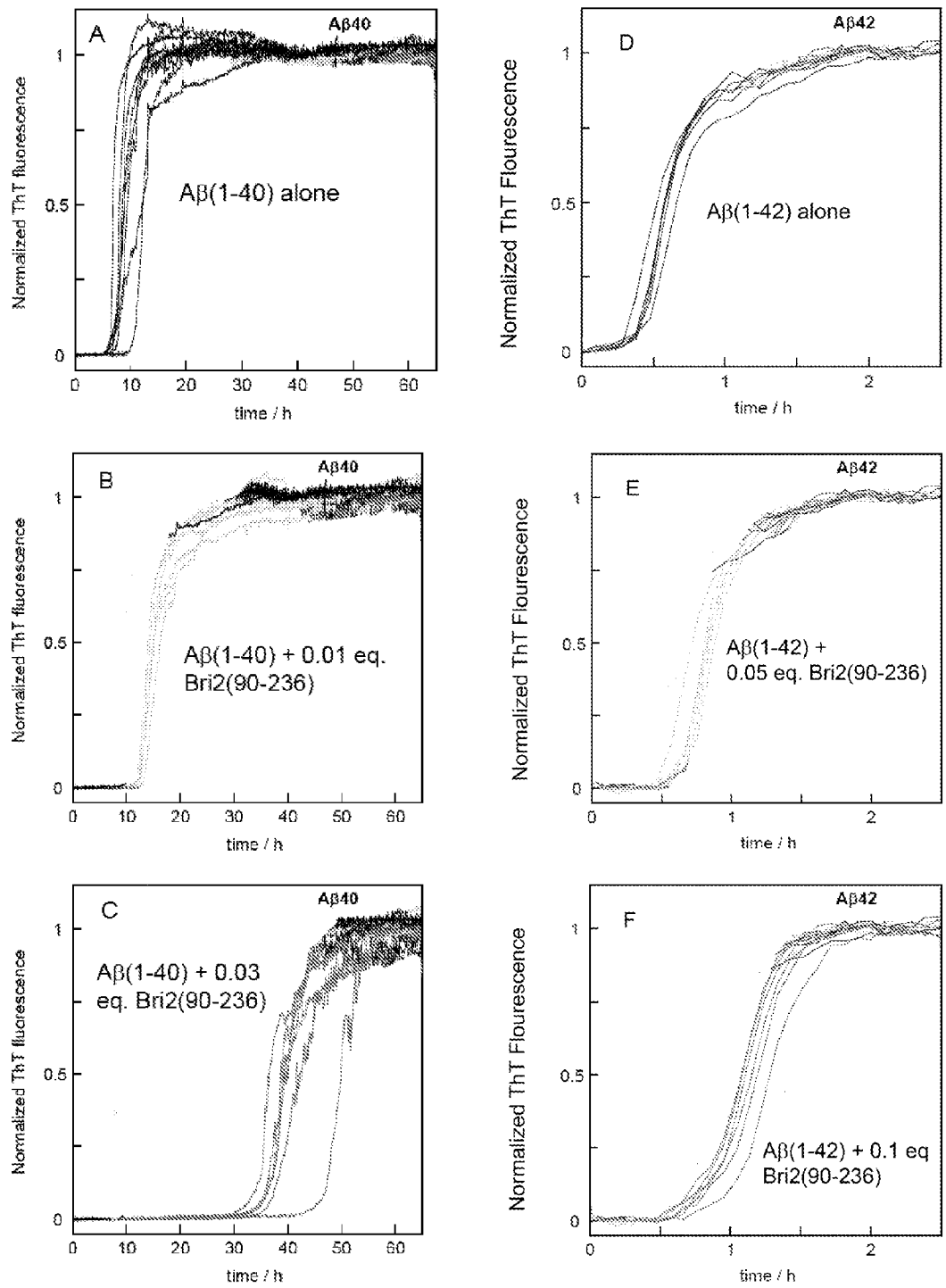
FIG. 10 shows effects of Bri2(90-236) (SEQ ID NO: 2) on $A\beta_{1-40}$ (SEQ ID NO: 11) (A-C) and $A\beta_{1-42}$ (SEQ ID NO: 12) (D-F) fibril formation in a Thioflavin T (ThT) fluorescence assay.

ThT was used as a reporter on fibril formation in kinetic experiments monitoring ThT fluorescence as a function of time for Aβ alone or Aβ with different concentrations of the Bri2(90-236) proteins. Examples of aggregation kinetics for Aβ$_{1-40}$ alone and with 0.01 or 0.03 molar equivalents of Bri2(90-236) are shown in FIG. 10A-C, respectively. Clearly, the lag time for Aβ$_{1-40}$ aggregation increases extensively in the presence of Bri2(90-236), while the elongation rate is largely unaffected. Very large effects on the lag time are observed far below equimolar concentration of Bri2(90-236) relative to Aβ$_{1-40}$. The mid-point of the aggregation process, $t_{1/2}$, was obtained from each kinetic trace by fitting a sigmoidal function to the data. The half time increased from 9.0±0.6 h for 6 µM Aβ$_{1-40}$ alone to 14.2±0.2 for 6 µM Aβ with 60 nM Bri2(90-236). In the presence of 170 nM Bri2(90-236), the half time was prolonged approximately 4.5 times to 40.5±2.0 h. The retarding effect increases with increasing Bri2-Brichos concentration, and above a molar ratio of 0.1 (1 Bri2(90-236) per 10 Aβ$_{1-40}$ molecules) the lag time exceeds one week and becomes practically difficult to quantify.

Examples of kinetic traces by ThT fluorescence for Aβ$_{1-42}$ alone and with 0.05 and 0.1 molar equivalents of Bri2(90-236) are shown in FIG. 10D-F, respectively. Bri2(90-236) retards the aggregation of Aβ$_{1-42}$ below equimolar amounts of the Bri2(90-236) protein. At a molar ratio of 0.1 (1 Bri2(90-236) per 10 Aβ$_{1-42}$), the lag time and half time are doubled compared to the undisturbed case, while the elongation rate is similar in all cases. Although strong effects are seen on Aβ$_{1-42}$ aggregation kinetics, it is clear that higher concentrations of the Bri2(90-236) proteins are needed to exert the same effect as on Aβ$_{1-40}$ aggregation.

Control experiments were set up to study the aggregation kinetics of Aβ$_{1-40}$ and Aβ$_{1-42}$ in the presence of the three proteins anti-thrombin, cystatin and a single chain monellin variant. Each control-protein was added at 0.1 and 1 molar equivalents to Aβ$_{1-40}$ as well as Aβ$_{1-42}$, and aggregation was followed by the ThT assay. In all cases, the effects observed on Aβ aggregation were small compared to those seen for the same amounts of Bri2(90-236) (data not shown).

Aggregation of 8 µM Aβ$_{1-40}$ was monitored by recording the ThT fluorescence intensity as a function of time in 20 mM Na-phosphate, 200 µM EDTA, 20 µM ThT, 0.02% NaN$_3$, 37° C. with 100 rpm shaking. 800 nM Bri2(90-236) was added from a concentrated stock before the start of the experiment or at different time points after starting the experiment ranging from 0.3 to 11.2 hours. Clearly, the aggregation process can be delayed by Bri2(90-236) protein if added anywhere during the lag time. If Bri2(90-236) is added during the early part of the sigmoidal transition, the process appears to halt with no further growth of the ThT positive aggregates. When added close to the mid point of the transition, the Bri2(90-236) protein causes the process to reduce its speed and progress at lower rate. When added at the end of the transition, no effect is seen.

The invention claimed is:

1. A method for therapeutically treating or delaying the progression of a condition selected from the group consisting of Alzheimer's disease, familial Danish dementia and familial British dementia in a mammal in need thereof, the method comprising administering to said mammal a therapeutically effective amount of an isolated protein, wherein the isolated protein decreases or reduces amyloid fibril formation and aggregation of amyloid β peptide, and wherein the isolated protein is selected from the group consisting of proteins comprising an amino acid sequence having at least 70% identity to residues 90-236 of Bri2 from human (SEQ ID NO: 2); and proteins comprising an amino acid sequence having at least 70% identity to any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10); with the provisos that said protein is not comprising an amino acid sequence having at least 70% identity to residues 1-89 of Bri2 from human (SEQ ID NO: 3); and said protein is not comprising an amino acid sequence having at least 70% identity to human ABri23 (SEQ ID NO: 4).

2. The method according to claim 1, wherein the isolated protein is selected from the group consisting of proteins comprising an amino acid sequence having at least 70% identity to residues 90-236 of Bri2 from human (SEQ ID NO: 2); and proteins comprising an amino acid sequence having at least 70% identity to the Brichos domain of Bri2 from human (SEQ ID NO: 5).

3. The method according to claim 1, wherein the isolated protein is selected from the group consisting of proteins comprising an amino acid sequence having at least 90% identity to any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10).

4. The method according to claim 3, wherein the isolated protein is selected from the group consisting of proteins comprising any one of the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10).

5. The method according to claim 1, wherein the isolated protein consists of less than or equal to 200 amino acid residues.

6. The method according to claim 5, wherein the isolated protein consists of less than or equal to 150 amino acid residues.

7. The method according to claim 6, wherein the isolated protein consists of more than or equal to 90 amino acid residues.

8. The method according to claim 1, wherein the condition is Alzheimer's disease.

9. The method according to claim 1, wherein the mammal is a human.

10. The method according to claim 1, wherein the isolated protein is selected from the group of proteins consisting of residues 90-236 of Bri2 from human (SEQ ID NO: 2) and the Brichos domains of Bri2 from human (SEQ ID NO: 5), chimpanzee (SEQ ID NO: 6), bovine (SEQ ID NO: 7), pig (SEQ ID NO: 8), mouse (SEQ ID NO: 9) and rat (SEQ ID NO: 10).

11. The method according to claim 10, wherein the isolated protein is selected from the group of proteins consisting of residues 90-236 of Bri2 from human (SEQ ID NO: 2); and the Brichos domain of Bri2 from human (SEQ ID NO: 5).

12. The method according to claim 11, wherein the isolated protein consists of residues 90-236 of Bri2 from human (SEQ ID NO: 2).

13. The method according to claim 11, wherein the isolated protein consists of the Brichos domain of Bri2 from human (SEQ ID NO: 5).

* * * * *

SEQUENCE LISTING

<160> NUMBER OF SEQ ID NOS: 15

<210> SEQ ID NO 1
<211> LENGTH: 266
<212> TYPE: PRT
<213> ORGANISM: Homo sapiens

<400> SEQUENCE: 1

```
Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110
```

```
Gln Thr Ile Glu Glu Asn Ile Lys Ile Phe Glu Glu Val Glu
        115                 120                 125

Phe Ile Ser Val Pro Val Pro Glu Phe Ala Asp Ser Asp Pro Ala Asn
130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
        195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Ser
                260                 265

<210> SEQ ID NO 2
<211> LENGTH: 147
<212> TYPE: PRT
<213> ORGANISM: Homo sapiens

<400> SEQUENCE: 2

Gly Ile Lys Tyr Ile Lys Asp Asp Val Ile Leu Asn Glu Pro Ser Ala
1               5                   10                  15

Asp Ala Pro Ala Ala Leu Tyr Gln Thr Ile Glu Glu Asn Ile Lys Ile
                20                  25                  30

Phe Glu Glu Glu Val Glu Phe Ile Ser Val Pro Val Pro Glu Phe
            35                  40                  45

Ala Asp Ser Asp Pro Ala Asn Ile Val His Asp Phe Asn Lys Lys Leu
50                  55                  60

Thr Ala Tyr Leu Asp Leu Asn Leu Asp Lys Cys Tyr Val Ile Pro Leu
65                  70                  75                  80

Asn Thr Ser Ile Val Met Pro Pro Arg Asn Leu Leu Glu Leu Leu Ile
                85                  90                  95

Asn Ile Lys Ala Gly Thr Tyr Leu Pro Gln Ser Tyr Leu Ile His Glu
                100                 105                 110

His Met Val Ile Thr Asp Arg Ile Glu Asn Ile Asp His Leu Gly Phe
            115                 120                 125

Phe Ile Tyr Arg Leu Cys His Asp Lys Glu Thr Tyr Lys Leu Gln Arg
130                 135                 140

Arg Glu Thr
145

<210> SEQ ID NO 3
<211> LENGTH: 89
<212> TYPE: PRT
<213> ORGANISM: Homo sapiens

<400> SEQUENCE: 3

Met Val Lys Val Thr Phe Asn Ser Ala Leu Ala Gln Lys Glu Ala Lys
1               5                   10                  15
```

```
Lys Asp Glu Pro Lys Ser Gly Glu Glu Ala Leu Ile Ile Pro Pro Asp
                20                  25                  30

Ala Val Ala Val Asp Cys Lys Asp Pro Asp Val Val Pro Val Gly
         35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys
                85
```

```
<210> SEQ ID NO 4
<211> LENGTH: 23
<212> TYPE: PRT
<213> ORGANISM: Homo sapiens

<400> SEQUENCE: 4
```

```
Glu Ala Ser Asn Cys Phe Ala Ile Arg His Phe Glu Asn Lys Phe Ala
1               5                   10                  15

Val Glu Thr Leu Ile Cys Ser
                20
```

```
<210> SEQ ID NO 5
<211> LENGTH: 95
<212> TYPE: PRT
<213> ORGANISM: Homo sapiens

<400> SEQUENCE: 5
```

```
Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
                20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Ile Asp His Leu Gly
65                  70                  75                  80

Phe Phe Ile Tyr Arg Leu Cys His Asp Lys Glu Thr Tyr Lys Leu
                85                  90                  95
```

```
<210> SEQ ID NO 6
<211> LENGTH: 95
<212> TYPE: PRT
<213> ORGANISM: Pan troglodytes

<400> SEQUENCE: 6
```

```
Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
                20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Ile Asp His Leu Gly
65                  70                  75                  80

Phe Phe Ile Tyr Arg Leu Cys His Asp Lys Glu Thr Tyr Lys Leu
```

<210> SEQ ID NO 7
<211> LENGTH: 95
<212> TYPE: PRT
<213> ORGANISM: Bos taurus

<400> SEQUENCE: 7

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Lys Asn Leu Leu Glu Leu Leu
        35                  40                  45

Ile Asn Ile Lys Ala Gly Thr Tyr Leu Pro Gln Ser Tyr Leu Ile His
    50                  55                  60

Glu His Met Val Ile Thr Asp Arg Ile Glu Asn Ile Asp His Leu Gly
65                  70                  75                  80

Phe Tyr Ile Tyr Arg Leu Cys His Asp Lys Glu Thr Tyr Lys Leu
                85                  90                  95

<210> SEQ ID NO 8
<211> LENGTH: 95
<212> TYPE: PRT
<213> ORGANISM: Sus scrofa

<400> SEQUENCE: 8

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Arg Asn Leu Leu Glu Leu Leu
        35                  40                  45

Ile Asn Ile Lys Ala Gly Thr Tyr Leu Pro Gln Ser Tyr Leu Ile His
    50                  55                  60

Glu His Met Val Ile Thr Asp Arg Ile Glu Asn Ile Asp His Leu Gly
65                  70                  75                  80

Phe Tyr Ile Tyr Arg Leu Cys His Asp Lys Glu Thr Tyr Lys Leu
                85                  90                  95

<210> SEQ ID NO 9
<211> LENGTH: 95
<212> TYPE: PRT
<213> ORGANISM: Mus musculus

<400> SEQUENCE: 9

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Lys Asn Leu Leu Glu Leu Leu
        35                  40                  45

Ile Asn Ile Lys Ala Gly Thr Tyr Leu Pro Gln Ser Tyr Leu Ile His
    50                  55                  60

Glu His Met Val Ile Thr Asp Arg Ile Glu Asn Val Asp Asn Leu Gly
65                  70                  75                  80

Phe Phe Ile Tyr Arg Leu Cys His Asp Lys Glu Thr Tyr Lys Leu
                85                  90                  95

```
<210> SEQ ID NO 10
<211> LENGTH: 95
<212> TYPE: PRT
<213> ORGANISM: Rattus norvegicus

<400> SEQUENCE: 10

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Arg Asn Leu Leu Glu Leu Leu
        35                  40                  45

Ile Asn Ile Lys Ala Gly Thr Tyr Leu Pro Gln Ser Tyr Leu Ile His
    50                  55                  60

Glu His Met Val Ile Thr Asp Arg Ile Glu Asn Val Asp His Leu Gly
65                  70                  75                  80

Phe Phe Ile Tyr Arg Leu Cys His Asp Lys Glu Thr Tyr Lys Leu
                85                  90                  95

<210> SEQ ID NO 11
<211> LENGTH: 40
<212> TYPE: PRT
<213> ORGANISM: Homo sapiens

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 12
<211> LENGTH: 42
<212> TYPE: PRT
<213> ORGANISM: Homo sapiens

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 13
<211> LENGTH: 15
<212> TYPE: DNA
<213> ORGANISM: Homo sapiens

<400> SEQUENCE: 13
ggtgccatgg gaata                                                15

<210> SEQ ID NO 14
<211> LENGTH: 15
<212> TYPE: DNA
<213> ORGANISM: Homo sapiens

<400> SEQUENCE: 14
```

```
ctctagagga tccct                                               15

<210> SEQ ID NO 15
<211> LENGTH: 12
<212> TYPE: PRT
<213> ORGANISM: Artificial Sequence
<220> FEATURE:
<223> OTHER INFORMATION: synthetic peptide

<400> SEQUENCE: 15

Lys Phe Phe Glu Tyr Asn Gly Lys Lys Phe Phe Glu
1               5                   10
```